United States Patent [19]

Forrow et al.

[11] Patent Number: 5,710,011

[45] Date of Patent: Jan. 20, 1998

[54] MEDIATORS TO OXIDOREDUCTASE ENZYMES

[75] Inventors: Nigel Forrow, Abingdon; Stephen Walters, Kirtlington, both of England

[73] Assignee: Medisense, Inc., Waltham, Mass.

[21] Appl. No.: 400,133

[22] Filed: Mar. 6, 1995

Related U.S. Application Data

[63] Continuation of Ser. No. 98,375, Aug. 9, 1993, abandoned.

[30] Foreign Application Priority Data

Jun. 5, 1992 [GB] United Kingdom ............... 9212010

[51] Int. Cl.$^6$ ............... C12Q 1/26; C12Q 1/00; C12Q 1/32; G01N 33/566

[52] U.S. Cl. ............... 435/25; 435/4; 435/14; 435/817; 435/23; 435/26; 435/28; 436/501; 436/801; 436/73; 436/74

[58] Field of Search ............... 435/25, 4, 14, 435/817, 23, 26, 28; 436/501, 801, 73, 74; 536/103

[56] References Cited

U.S. PATENT DOCUMENTS

| | | | |
|---|---|---|---|
| 4,243,751 | 1/1981 | Swartz | 435/168 |
| 4,514,276 | 4/1985 | Covington et al. | 204/403 |
| 4,591,550 | 5/1986 | Hafeman et al. | 435/25 |
| 4,711,245 | 12/1987 | Higgins et al. | 435/25 |
| 4,713,347 | 12/1987 | Mitchell et al. | 435/25 |
| 4,963,815 | 10/1990 | Hafeman et al. | 435/25 |
| 4,978,610 | 12/1990 | Forrest et al. | 435/25 |
| 5,126,034 | 6/1992 | Carter et al. | 204/403 |
| 5,149,630 | 9/1992 | Forrest et al. | 435/25 |
| 5,286,362 | 2/1994 | Hoenes et al. | 204/403 |

FOREIGN PATENT DOCUMENTS

| | | |
|---|---|---|
| 2080840 | 2/1992 | Canada. |
| 0 078 636 | 5/1983 | European Pat. Off.. |
| 0 125 136 | 11/1984 | European Pat. Off.. |
| 0 125 137 | 11/1984 | European Pat. Off.. |
| 0 125 139 | 11/1984 | European Pat. Off.. |
| 0 125 867 | 11/1984 | European Pat. Off.. |
| 0 127 958 | 12/1984 | European Pat. Off.. |
| 0150602 | 8/1985 | European Pat. Off.. |
| 0 230 786 | 8/1987 | European Pat. Off.. |
| 9204466 | 3/1992 | WIPO. |

OTHER PUBLICATIONS

J. Org. Chem. 1991, 56, 35–41 (Isnin et al).
Inorganic Chem. 1969, vol. 8, No. 6, pp. 1340–1347 (McCleverty et al).
(Reger et al) Jour. Organometallic Chem, 170 (1979) 217–227.
(Hendry et al) Jour Biotech, vol. 15, No. 3, (1990) 229–238.
Rong et al. (Abstract)("Artifical Redox Enzymes") 1987.
J. Electroanal. Chem., (1988) 27–43.
J. Electroanal. Chem., 190 (1985) 117.
Anal. Chem., 56 (1987) 667.
Prog. React. Kinet., 16 (1991) 55.

(List continued on next page.)

*Primary Examiner*—John Kight
*Assistant Examiner*—Louise N. Leary
*Attorney, Agent, or Firm*—Fish & Richardson P.C.

[57] ABSTRACT

Half-sandwich complexes of transition metals having a single π-ligand with delocalised π bonding are of use in mediating electron transfer between an electrode and a redox protein, for example an oxidoreductase enzyme such as in an amperometric enzyme sensor. Suitable compounds include complexes of the general formula:

$$(\pi\text{-ligand})M(\text{not-}\pi\text{-ligand})_n$$

wherein the complex is charged or neutral, π-ligand represents the single π-bonded ligand, M represents the transition metal atom, n is the number of ligands which are not π-ligands, and the n not-π-ligands are the same or different, are univalent or multivalent, and serve to satisfy the valency of the transitional metal M.

36 Claims, 4 Drawing Sheets

OTHER PUBLICATIONS

Biosensors, 2 (1986) 71.
J. Organomet. Chem., 101 (1975) C43.
J. Electroanal. Chem. 201 (1986) 1.
J. Chem. Soc (a), (1970) 850.
J. Organomet. Chem., 56 (1973) 345.
Inorg. Chem., 6 (1967) 469.
J. Electroanal. Chem., 293 (1990) 55.
J. Chem. Soc. Dalton Trans., (1973) 1768.
Inorg. Chem., 5 (1966) 1157.
Bioelectrochem. Bioenerg., 24 (1990) 257.
Anal. Chem., 59 (1987) 666.
Anal. Chem., 62 (1990) 2429.
Electrochemical Sensors for Biomedical Applications, editor C.K.N. Lim, The Electrochem. Soc. (Proceedings Volume), 86–14 (1986) 16.
Inorg. Synth., 19 (1979) 154.

MEDIATORS TO OXIDOREDUCTASE ENZYMES

This is a continuation of application Ser. No. 08/098,375, filed Aug. 9, 1993 now abandoned.

The present invention relates to mediators to oxidoreductase enzymes. In particular, the present invention relates to such mediators for use in amperometric enzyme electrodes.

BACKGROUND OF THE INVENTION

Amperometric enzyme electrodes are described, for example, in BIOSENSORS Fundamentals and Applications, edited by Turner, Karube and Wilson, Oxford University Press (1987). The reader is referred to this book for background reading.

Electrical communication between an electrode and the active site of a redox enzyme is a key feature of amperometric enzyme electrodes. Generally this has been achieved using low molecular weight, rapidly diffusing mediators with fast redox couples. Organic compounds such as phenazine methosulphate, 2,6-dichloroindophenol, quinones and phenylene diamines were among the first such species to be used in conjunction with glucose oxidase (GOD). However, these compounds suffer from a number of problems which include poor stability and pH-dependent redox potentials. These problems have been addressed through the use of inorganic species such as octacyanotungstate, hexacyanoferrate, hexacyanoruthenate, ruthenium amine complexes, osmium complexes, and metal porphyrins.

Metal bipyridine and phenanthroline complexes have also been suggested. Many of these inorganic mediators suffer from the problem that it is not easy to modify their redox potentials and/or aqueous solubility. In this respect the field of inorganic mediators has been extended by ferrocenes, which are sandwich compounds with an iron atom sandwiched between two π-bonding cyclopentadienyl rings. The access to a large number of derivatives means that the properties of ferrocenes can readily be modified by substitution on one or both of the cyclopentadienyl rings.

Ferrocene mediators have been shown to undergo rapid electron transfer with oxidoreductase enzymes such as glucose oxidase (Anal. Chem., 56 (1987) 667); cholesterol oxidase (Electrochemical Sensors for Biomedical Applications, editor C. K. N. Lim, The Electrochem. Soc. (Proceedings Volume), 86–14 (1986) 16); sarcosine oxidase (J. Electroanal. Chem., 240 (1988) 33); lactate oxidase (J. Electroanal. Chem., 240 (1988) 33); pyruvate oxidase (J. Electroanal. Chem., 190 (1985) 117); xanthine oxidase (J. Electroanal. Chem., 190 (1985) 117); glutathione reductase (J. Electroanal. Chem., 190 (1985) 117); diaphorase (Electrochemical Sensors for Biomedical Applications, editor. C. K. N. Lim, The Electrochem. Soc. (Proceedings Volume), 86–14 (1986) 16); glucose dehydrogenase (Biosensors, 2 (1986) 71); and horseradish peroxidase (J. Electroanal. Chem., 201 (1986) 1).

Nevertheless, the need remains to expand the list of candidate mediator compounds, allowing new mediators to be developed with tailored properties suited to particular applications.

OBJECTS OF THE PRESENT INVENTION

A principal object of the present invention is the provision of compounds of use as mediators for oxidoreductase enzymes or other electron transfer redox proteins. Related objects include mediation processes employing such mediators, products based on the mediation processes, manufacturing methods for the mediated products, and compositions containing the mediators.

SUMMARY OF THE PRESENT INVENTION

It has now been found that complexes (half-sandwich complexes) of transition metals such as iron, manganese and chromium containing a single π-ligand (which may be allyl, cyclopropenyl, cyclobutadiene, cyclopentadienyl, benzene, cycloheptatrienyl or trimethylenemethane, among others) are capable of mediating electron transfer to oxidoreductase enzymes such as glucose oxidase, with efficiencies comparable to the ferrocenes but offering the potential for more extensive substitution chemistry. The mediating function is not restricted to enzymes, and may be used with other electron transfer redox proteins.

There have been some reports on the electrochemistry of transition metal half-sandwich complexes, but not in the context of mediation to redox proteins. For example, the effect of substitution on the electrochemical oxidation in acetonitrile of cyclopentadienyltricarbonyl-manganese and -rhenium is reported in J. Organomet. Chem., 101 (1975) C43. The voltammetric oxidation in dichloromethane of arene, cycloheptatriene, and cycloheptatrienyl tricarbonyl complexes of chromium is reported in J. Chem. Soc. Dalton Trans., (1973) 1768. Cyclic voltammetry in acetonitrile of a cyclopentadienylmanganese derivative, a cycloheptatrienyl-molybdenum derivative and a cyclopentadienyliron derivative is reported in J. Organomet. Chem., 170 (1979) 217. The voltammetric properties in dichloromethane of certain π-cyclopentadienylsulphur complexes of manganese, molybdenum, tungsten and cobalt are reported in Inorg. Chem., 8 (1969) 1340.

PREFERRED EMBODIMENTS OF THE INVENTION

In general, the present invention provides transition metal half-sandwich complexes, for use as mediators in electron transfer between enzymes and electrodes. Correspondingly, the present invention provides a process for mediating electron transfer between an oxidoreductase enzyme and an electrode, which is characterised by the use of a transition metal half-sandwich compound as mediator. We have found that such transition metal half-sandwich compounds can act as mediators in aqueous systems.

In another aspect, the present invention provides mediated enzyme products and methods of manufacturing such products. Illustratively the present complexes can be used in the manufacture of amperometric enzyme sensors, such as those of the kind described in EP-78636-A, EP 125136-A, EP 125137-A, EP 125139-A, EP 125867-A, EP 127958-A or EP 230786-A, but using a transition metal half-sandwich compound as mediator. The reader is referred to these published patent specifications, whose content is incorporated herein by reference. Accordingly, the present invention provides amperometric enzyme sensors of use for testing for the presence of an analyte in a sample, especially an aqueous sample. For example, the sample can be a complex biological sample, for instance a biological fluid such as whole blood, plasma or serum, and the analyte can be a naturally occurring metabolite such as glucose or cholesterol, or an introduced substance such as a drug.

Of particular utility for the manufacture of amperometric enzyme sensors, the present invention further provides an electrically conductive printing ink which includes a transition metal half-sandwich mediator compound.

A central feature of the invention is the use as a redox mediator for oxidoreductase enzymes of a half-sandwich complex where a single π-ligand is bonded to a transition metal ion complexed by other ligands. The single π-ligand will comprise 3 or more atoms, typically 3 to 7 atoms, which will generally be carbon but can include any heteroatom capable of π bonding including nitrogen, oxygen, sulphur and phosphorus. By definition in order to have π-bonding, at least three interlinked atoms of the π-ligand define a plane with delocalised π bonding and which interact directly with the transition metal atom. The nature of the transition metal ion is not critical, except for the ability to undergo rapid electron transfer. The identity of the other ligands is not critical, except that they are not π-bonding. For example, the other ligands may be chosen from any of carbonyl, phosphine, isocyanide, nitrosyl, bipyridine, phenanthroline or dithiolate.

Preferably, the half-sandwich compound for use as mediator is a complex of the general formula:

(π-ligand)M(not-π-ligand)$_n$ wherein the complex may be charged or neutral, π-ligand represents the single π-bonded ligand, M represents the transition metal atom, n is the number of ligands which are not π-ligands, and the n not-π-ligands are the same or different, are univalent or multivalent, and serve to satisfy the valency of the transitional metal M.

More preferably, the π-ligand is selected from π-ligands with 3 to 7 carbon atoms, and is most preferably an allyl, cyclopropenyl, cyclobutadiene, cyclopentadienyl, benzene, cycloheptatrienyl or trimethylenemethane group. The π-ligand can be unsubstituted, but is preferably a substituted ligand. The nature of the substituent is not critical, since it is a feature of the present invention that variation in the identity of the substituent allows the preparation of compounds with different properties for assessment as candidate mediators. Purely by way of illustration, there can be 1 or more, usually 1 to 4, substituents. Such substituents may be selected from alkyl groups, especially a methyl or ethyl group; alkoxy groups, especially a methoxy or ethoxy group; amino and substituted amino groups, especially an amino, dimethylamino, diethylamino or di(β-hydroxyethyl) amino group; aminoalkyl and substituted aminoalkyl groups, especially an aminomethyl or dimethylaminomethyl group; a carboxylic acid group; or a sulphonic acid group.

The transition metal M is preferably iron, manganese or chromium.

Each not-π-ligand is preferably selected from carbonyl, phosphine, isocyanide, nitrosyl, bipyridine, phenanthroline or dithiolate groups. The first four such groups are monovalent, while the last three such groups are divalent.

In one preferred form of the invention, the transition metal half-sandwich compound is employed as an inclusion complex in β-cyclodextrin, which typically takes the form of a 1:1 adduct.

The transition metal half-sandwich compounds are generally known or can be made by modified literature methods.

A particular advantage of transition metal half-sandwich complexes over the ferrocenes is that the greater degree of structural possibilities allows their properties to be tailored more closely to fit a particular enzyme application and/or biosensor configuration. Other applications and advantages of the present invention will be apparent, such as the possibility of the use of transition metal half-sandwich complexes as mediators to oxidoreductase enzymes, such as the generality of the flavoprotein, metalloprotein and quinoprotein oxidoreductases; also to act as mediators to redox proteins such as haemoglobin or to respiratory or other electron transfer redox proteins; the possibility of their use as labels for antigens or antibodies in immunochemical procedures including such as described in EP 125139-A; the possibility of their use as artificial substrates to monitor enzyme reactions with redox potentials modified by reaction with the enzyme; the possibility of tailoring the redox potential of a mediator by careful choice of ligands such that it may interact with a particular oxidoreductase protein but not with another; the use of the wider substitution chemistry of half sandwich complexes to fabricate enzyme-mediator complexes or modified electrodes; and other applications in the field of electrochemistry and bioelectrochemistry which will be apparent to the skilled person.

The preferred amperometric enzyme sensor adopting a transition metal half-sandwich compound as mediator utilizes a strip test element, especially a throw-away dry strip. For preference, a disposable test element carries a working electrode, the test reagents comprising at least the oxidoreductase enzyme and transition metal half-sandwich mediator compound for generation of a current indicative of the level of analyte, and a reference electrode. Typically, in the test element, the test reagents are in one or more carbon-based layers associated with the working electrode. Accordingly, the sensor electrodes preferably comprise electrode areas formed for instance by screen printing, spraying, or other suitable deposition technique.

For preference, respective carbon mixtures are applied on to a conductive track on a carrier, for example in close proximity to a reference electrode mixture connected to a second track. In this way, a sensor is produced which is capable of functioning with a small sample of whole blood or other liquid covering the effective electrode areas. The mixtures are most suitably applied to the carrier by screen printing.

In a particularly preferred embodiment, the present invention provides a dry strip sensor which comprises an elongate, electrically-insulating carrier having a pair of longitudinal, substantially parallel, electrically-conducting tracks thereupon, each track being provided at the same end with means for electrical connection to a read-out means and provided with an electrode, one of the electrodes being the reference electrode and the other being the working electrode, together with test reagents.

More especially, such a sensor is configured in the form of a supporting strip of electrically insulating carrier material such as a synthetic polymer (for instance pvc) carrying at a location between its ends the two electrodes supported on electrically conductive printed tracks. For example, the electrodes can take the form of two rectangular areas side by side on the carrier strip. Such areas can be configured as a target area to be covered by a single drop of sample, such as whole blood, for testing for an analyte. If desired, non-rectangular electrode areas, for instance diamond-shaped, semicircular, or triangular areas, can be employed to provide a target area for optimised contact by a liquid sample.

The carrier carries at least two electrodes, namely a reference electrode and a working electrode, but may carry further electrodes such as a counter electrode and/or a dummy electrode, which is of similar formulation to the working electrode with associated test reagents, but lacks one or more of its active components. Such a dummy third electrode can lead to more reliable results, in that if charge passed at the third electrode is subtracted from charge passed at the working electrode, then the resulting charge is solely due to the reaction of interest.

A membrane may be provided at and above the target to perform a filtration function, for example to filter blood cells from the sample before it enters the test strip. As an alternative, a filtration or cellular separation membrane might be cast in situ.

In a more particularly preferred embodiment, there is provided a single use disposable electrode strip for attachment to signal readout circuitry of a sensor system to detect a current representative of a compound in a liquid mixture, the strip comprising:

a) an elongated support adapted for releasable attachment to the readout circuitry;

b) a first conductor extending along the support and comprising a conductive element for connection to the readout circuitry;

c) an active electrode on the strip in contact with the first conductor and positioned to contact the mixture, the active electrode comprising a printed layer on the support, the printed layer comprising an enzyme capable of catalyzing a reaction involving a substrate for the enzyme and a transition metal half-sandwich mediator capable of transferring electrons transferred between the enzyme-catalyzed reaction and the first conductor to create a current representative of the activity of the enzyme and representative of the compound, the printed layer having an area less than 25 square mm;

d) a second conductor extending along the support, comprising a conductive element for connection to the readout circuitry; and e) a reference electrode in contact with the second conductive element and positioned to contact the mixture and the second conductor, the first conductive element and the active electrode being spaced apart from the second conductive element and the reference electrode, and the electrodes being sized and positioned to present a combined effective area small enough to be completely coverable by a drop of blood, whereby the blood completes an electrical circuit across the active electrode and the reference electrode, for amperometric detection of the activity of the enzyme.

The test strips of this invention can detect analytes for example by known mediated enzyme electrochemical reactions, but using a transition metal half-sandwich compound as mediator. In this respect, the reader is referred to European Patent 78636-A, especially for its mention of glucose oxidase, as well as European Patent 127958-A and European Patent Specification 125137-A. Other enzymes for use with the present mediators include combinations of cholesterol oxidase, a peroxidase and optionally cholesterol esterase, for detection of free or total cholesterol, as described in European Patent 230786-A; and more generally systems including oxidoreductase or other enzymes, including flavoproteins, quinoproteins, and metalloproteins, and one or more mediator compounds, for example as described in European Patent Specification 125137-A. Other enzyme systems suitable for use in devices according to the present invention include oxidoreductases using nicotinamide and adenine dinucleotide and nicotinamide adenine dinucleotide phosphate as cofactors, for example those described in European Patent 125867-A; or systems using more than one enzyme, as described in European Patent 125136-A.

Test strips according to this invention are intended for use with electronic apparatus and meter systems. These control the progress of the electrochemical reaction, for example by maintaining a particular potential at the electrodes, and monitor the reaction and calculate and present the result. A particular feature which is desirable in a meter system for use with test strips of this type is the capability to detect the wetting of the reaction zone by sample fluid; this allows timely initiation of the measurement and reduces the scope for inaccuracies caused by user error. It is possible to achieve this goal by applying a potential to the electrodes of the test strip as soon as it is inserted into the meter; this potential is maintained until a certain threshold current is measured which will reflect the wetting of the reaction zone by sample fluid. The potential may then be removed for a short time to allow wetting to be completed before initiation of measurement in the usual way.

A further feature which is advantageous is the facility to ascertain automatically the identity of test strips for the measurement of different analytes. This might be achieved, for example, by the provision of additional contacts on the test strip in a pattern characterising the type of strip; the meter would have contact pads to determine the presence or absence of each contact. Alternatively, a system is possible using one or more additional circuit loops printed on the test strip of determined resistance characteristic of the type of strip, as described in U.S. Pat. No. 5,126,034 at column 4, lines 3 to 17. As a further alternative, notches or other shapes might be made in the proximal end of the test strip which is inserted into the meter; switches or optical detectors in the meter can detect the presence or absence of each notch. Further possibilities for recognition of strip types include varying the colour of the strips and providing the meter with a photodetector capable of distinguishing the range of colours; also providing the strips with barcodes; magnetic stripes or other markings and providing the meter with a suitable reading arrangement.

A preferred technique for large scale production of test strips of the invention will be described. In this instance, the strip electrodes have a three-electrode configuration comprising a reference electrode, a working electrode, and a dummy electrode.

The carrier can be made from any material which has an electrically insulating surface including poly(vinyl chloride), polycarbonate, polyester, paper, cardboard, ceramic, metal coated with ceramic or other insulating substance. Poly(vinyl chloride) or a blend of polycarbonate/polyester seems to be particularly suitable.

A sheet of carrier material is cut to size using a punch tool which crops the outer edges at the same time as punching a number of registration holes. It is advantageous to use these holes during subsequent operations, but it is also feasible to edge-register throughout the process.

A conductive ink is applied to the carrier by a method of deposition such as screen printing. The punched holes are used to register the carrier. This layer produces the contact areas which allow a meter to interface with the test strip and provides an electrical circuit between the contacts and the active chemistry occurring on the strip. For preference, the ink is an organic solvent-based carbon mixture which is air-dried. Alternative formulations are possible including water-based inks and silver inks. Other methods of drying or curing the inks include infra-red, ultra-violet and radio-frequency radiation.

A layer forming the reference electrode is then printed with an organic solvent-based ink containing a silver/silver chloride mixture. The print extends to partially cover the middle track of the carbon print where it extends into the reaction zone. It is useful if separate parts of this print are extended to cover parts of the other carbon tracks outside the reaction zone so that the total electrical resistance of each track is reduced.

A layer of dielectric ink may optionally be printed to cover the majority of the printed carbon and silver/silver chloride layers. In this case, two areas are left uncovered, namely the electrical contact areas and the sensing area which will underlie the reactive zone. This print serves to define the area of the reactive zone, and to protect exposed tracks from short circuit.

For the working electrode, one or more inks are deposited to a precise thickness within a defined area on top of one of the conductive tracks within the reaction zone, to deposit the enzyme and the half-sandwich mediator compound. It is convenient to do this by means of screen printing. Other ways of laying down this ink include inkjet, volumetric dosing, gravure printing, flexographic printing, and letterpress printing.

Optionally, a second partially active ink forming a dummy electrode can be deposited on a remaining conductive track, such that each active ink lies on a conducting track equidistant from a central track coated with the silver/silver chloride ink.

EXAMPLES OF THE INVENTION

The present invention will now be further described by way of non-limiting examples.

All reactions and subsequent manipulations involving organometallic reagents were performed under anaerobic and anhydrous conditions using an atmosphere of nitrogen. Chromium hexacarbonyl and methylcyclopentadienyl manganese tricarbonyl were obtained from Strem Chemicals, Inc. 1,10-Phenanthroline, 2,2'-bipyridine, β-cyclodextrin hydrate, dimethyldithiocarbamic acid, diethyldithiocarbamic acid and 4-morpholinecarbodithioic acid were purchased from Aldrich Chemicals. Disodium cis 1,2-dicyanoethylene-1,2-dithiolate was prepared by a published method (Inorg. Chem., 5 (1966) 1157). The product compounds were designated by Compound numbers, as in "Compound 6".

The phosphate buffer solution (PBS) of 0.15 M phosphate (with 0.2 M sodium chloride as supporting electrolyte), pH 7.0, containing 0.1 M glucose was prepared using Analar reagents from Merck BDH. The solution was stored overnight at 4° C. prior to use to allow equilibration of the α- and β-anomers. Glucose oxidase (EC 1.1.3.4 from *Aspergillus niger*) was supplied by Sturge Enzymes. Horseradish peroxidase was obtained from Biozyme.

In the Examples, reference is made to the accompanying figures of the drawings.

EXAMPLE 1

Arene chromium tricarbonyl complexes were prepared by refluxing the appropriate arene with $Cr(CO)_6$ in refluxing di-n-butyl ether/tetrahydrofuran (10:1) according to a general literature procedure (Inorg. Synth., 19 (1979) 154). [MeCpMn(NO)(CO)$_2$]PF$_6$ Compound 9 was prepared by the procedure of King and Bisnette (Inorg. Chem., 6 (1967) 469). Literature methods were used for the synthesis of [MeCpMn(NO)(CN)$_2$]Na Compound 13 (J. Organomet. Chem., 170 (1979) 217), [MeCpMn(NO)(bipy)]PF$_6$ Compound 14 (Inorg. Chem., 8 (1969) 1340), [MeCpMn(NO)(phen)]PF$_6$ Compound 15 (Inorg. Chem., 8 (1969) 1340), [MeCpMn(NO)(S$_2$CNMe$_2$)] Compound 10 (Inorg. Chem., 8 (1969) 1340), [MeCpMn(NO)(S$_2$CNEt$_2$)] Compound 11 (Inorg. Chem., 8 (1969) 1340), and [MeCpMn(NO){(SCCN)$_2$}][NEt$_4$] Compound 16 (Inorg. Chem., 8 (1969) 1340).

Preparation of

[MeCpMn(NO)(S$_2$CNCH$_2$CH$_2$OCH$_2$CH$_2$)]

Compound 12:

The salt [MeCpMn(NO)(CO)$_2$]PF$_6$ Compound 9 (1.5 g, 4.1 mmol) was dissolved in warm, degassed acetone (45 ml). The stirred solution was treated with a mixture of 4-morpholinecarbodithioic acid (1.03 g, 4.11 mmol) in 50 ml ethanol/acetone (1:1) and 15 ml water. A colour change to red-brown was observed together with the liberation of carbon monoxide gas. Stirring was continued for 2 hours at 45° C. Filtration yielded a solution from which a crude black-brown product was obtained by reduction of the solvent volume in vacuo followed by cooling. The resulting precipitate was filtered off and recrystallised from boiling petroleum ether (40°–60° C.)/acetone, giving brown needles of Compound 12 (0.2g, 15%)] after storage at –20° C. for 3 days.

Melting point: 112°–113° C.

Analysis:

Found: C,40.78; H,4.70; N,8.53.

Calc for $C_{11}H_{15}N_2O_2S_2Mn$: C,40.49; H,4.63; N,8.48

Preparation of [MeCpMn(NO)(S$_2$CNMe$_2$)]β-cyclodextrin:

The procedure used was adapted from a reported method for the preparation of ferrocene-β-cyclodextrin adducts (J. Chem. Soc. Dalton Trans, (1991) 2749).

β-Cyclodextrin hydrate (2.50 g, 2.2 mmol) was dissolved in water (25 ml) at 70° C. under nitrogen. Solid [MeCpMn(NO)(S$_2$CNMe$_2$)] Compound 10 (0.284 g, 1.0 mmol) was then added and the resulting mixture was stirred and heated at 70° C. for 7 hours. Upon cooling, the precipitate was filtered off and washed copiously with water followed by ethanol and diethyl ether. The required adduct (0.405 g) was obtained as a brown powder, melting point 300° C. with decomposition. Initial microanalysis results on the crude product indicate that it is a 1:1 adduct containing several molecules of water of crystallisation.

EXAMPLE 2

The half wave potential of benzene chromium tricarbonyl has been recorded as +710 mV vs SCE in dichloromethane (J. Chem Soc. Dalton Trans., (1973) 1768). This complex has negligible solubility in buffer. Derivatives, however, are simple to prepare in good yield using the thermolysis of chromium hexacarbonyl with substituted benzenes in tetrahydrofuran/di-n-butyl ether (Inorg. Synth., 19 (1979) 154). Arenes containing amines directly attached to the ring were selected in the hope of enhancing the aqueous solubility of the resulting complexes as well as reducing their mid-point potentials. A series of seven complexes were investigated and were found to demonstrate aqueous electrochemistry in the region +280 to +40 mV, as shown in the following table.

| Arene ligand | Compound | $E_{ox}$ (mV) |
|---|---|---|
| $C_6H_5NMe_2$ | 1 | +250 |
| 1,4-$MeC_6H_4NH_2$ | 2 | +280 |
| $C_6H_5N(CH_2CH_2OH_2)$ | 3 | +250 |
| 1,4-$C_6H_4(NH_2)_2$ | 4 | +135 |
| 2,4,-$(MeO)_2C_6H_3NH_2$ | 5 | +170 |
| 1,4,-$C_6Me_4(NH_2)_2$ | 6 | +40 |
| 1,3,5-$C_6H_3(NH_2)_3$ | 7 | +50 |

Figure 1:
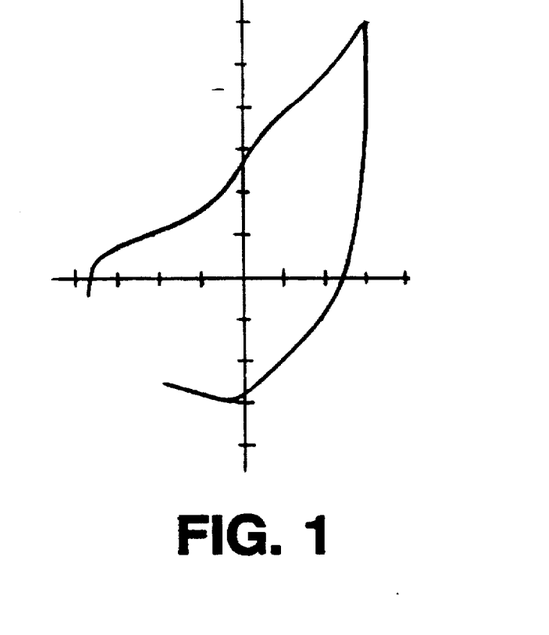
FIG. 1 is a cyclic voltammogram of the chromium complex Compound 6.

FIG. 1 is a cyclic voltammogram of the chromium complex Compound 6, at 50 mV/s in PBS. Compound 6 was the only compound to display a reversible wave, as shown FIG. 1, though it was poorly soluble in aqueous buffer. Further studies were confined to Compound 6.

EXAMPLE 3

Figure 2A:
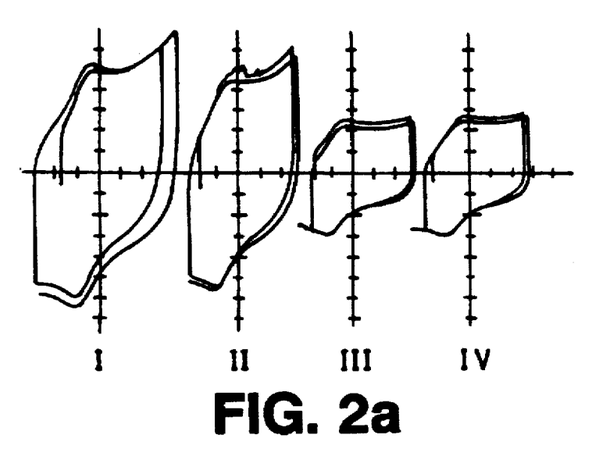
FIG. 2a comprises cyclic voltammograms of electrodes containing the chromium complex Compound 6, and 2b the catalytic wave upon addition of glucose oxidase.
Figure 2B:
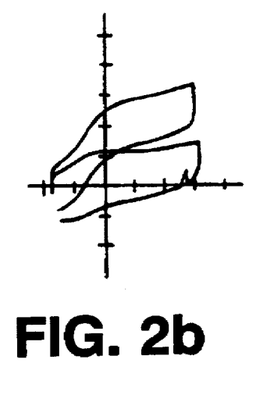

Screen-printed electrodes incorporating Compound 6 were produced from an organic carbon ink containing the chromium complex at a level of 3.5 mg/g ink. FIG. 2a comprises cyclic voltammograms of electrodes containing the chromium complex Compound 6 at 50 mV/s and 0.2 µA/cm in PBS, and FIG. 2b the catalytic wave upon addition of 100 µl glucose oxidase recorded at 20 mV/s and 0.5 µA/cm. It will be seen from FIG. 2a that a reversible wave was recorded when PBS was applied to the electrodes, but at a lower mid-point potential of −15 mV. From FIG. 2b, it is seen that GOD mediation occurs on applying mixtures of enzyme and glucose to the electrodes, with small catalytic currents of about 1 µA.

The result is significant since it demonstrates that it is possible to use a very hydrophobic complex to mediate to GOD when it is incorporated in a carbon electrode. It also illustrates the potential of transition metal half-sandwich complexes as mediators.

EXAMPLE 4

Manganese half-sandwich complexes can be obtained from (methylcyclopentadienyl)manganese tricarbonyl Compound 8, an inexpensive and readily available starting material due to its large scale use as an anti-knocking additive in unleaded petrol. For example, as shown in the following reaction scheme, access to a wide and varied carbonyl substitution chemistry is provided via the nitrosyl cation Compound 9 produced by treatment of the tricarbonyl compound Compound 8 with nitrous acid (Inorg. Chem., 6 (1967) 469) or nitrosonium ion (J. Organomet. Chem, 56 (1973) 345).

Figure 3A:
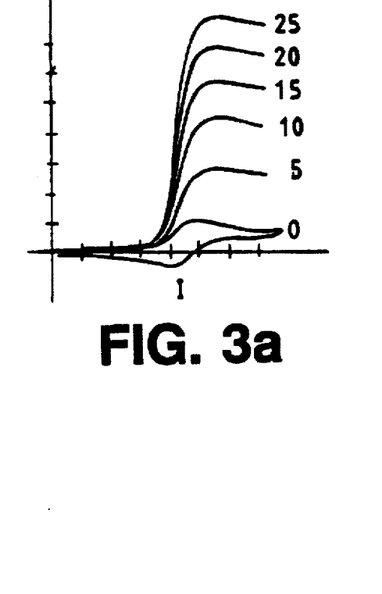
FIG. 3a and 3b show catalytic waves obtained on titrating glucose oxidase with the manganese complex Compound 8.
Figure 3B:
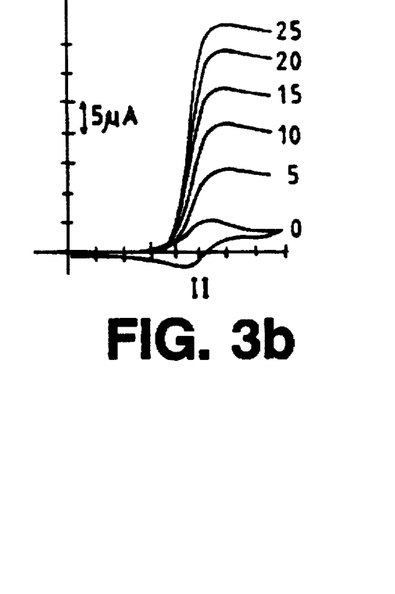
Figure 4:
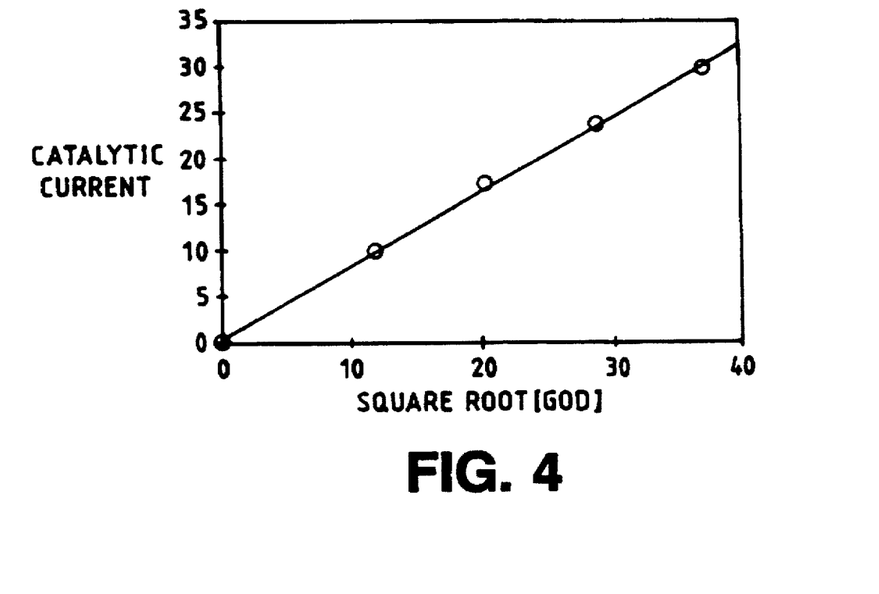
FIG. 4 is a graphical plot of data obtained from the catalytic waves of FIG. 3.

Reaction Scheme:

-continued
Reaction Scheme:

Cyclopentadienyl manganese tricarbonyl itself is more difficult to oxidise than ferrocene; its oxidation potential being some 1.2 V more positive than ferrocene in acetonitrile (J. Organomet. Chem., 101 (1975) C43). The nitrosyl cation Compound 9 readily decomposes in aqueous buffer to give a species which is irreversibly oxidized at +230 mV. However, treatment of Compound 8 with cyanide ion (J. Organomet. Chem., 170 (1979) 217) affords the anionic dicyano complex Compound 13 which is highly water soluble and displays a reversible wave at +440 mV. FIGS. 3a and 3b show catalytic waves obtained at 5 mV/s and 5 µA/cm on titrating glucose oxidase with the manganese complex Compound 8, using 0 to 25 µl GOD titrated into a solution of Compound 8 in 0.1 M glucose/PBS. A series of catalytic waves of increasing amplitude were obtained. A second order rate coefficient for the oxidation of reduced GOD of $2.1 \times 10^5 \, M^{-1}s^{-1}$ was derived from the graph shown in FIG. 4 of $i_{cat}$ versus $[GOD]^{1/2}$ plotted according to literature methods (Prog. React. Kinet., 16 (1991) 55, and J. Electroanal. Chem., 293 (1990) 55). This rate constant compares very favourably with those determined for ferrocenes, such as $2.0 \times 10^5 \, M^{-1}s^{-1}$ for ferrocene monocarboxylic acid (Anal. Chem., 56 (1984) 667).

EXAMPLE 5

Several other manganese half-sandwich compounds were prepared from Compound 9. Treatment of Compound 9 with the bidentate ligands 2,2,-bibyridine and 1,10-phenanthroline in accordance with a literature method (J. Chem. Soc (A), (1970) 850) afforded the cation Compounds 14 and 15, respectively. Both complexes exhibited irreversible electrochemistry at potentials of about +600 mV.

Figure 5:
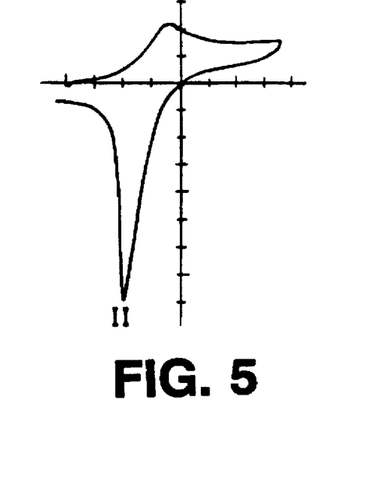
FIG. 5 is a cyclic voltammogram of the manganese complex Compound 16.

Compound 16 was prepared from cis-1,2-dicyanoethylene-1,2-dithiolate (Inorg. Chem., 8 (1969) 1340). FIG. 5 is a cyclic voltammogram of the manganese complex Compound 16 0.6 mM in PBS at 50 mV/s and 2 µA/cm. A much lower $E_{ox}$ of −25 mV was observed for the anionic dithiolene complex, but the oxidized form (a neutral species) proved to be insoluble in buffer. The resultant coating of the electrode meant that an enzyme titration was not possible.

The dithiocarbamate complexes Compounds 10 and 11 were prepared according to the literature method (Inorg. Chem., 8 (1969) 1340) which was also used to prepare the morpholinodithiocarbamate complex Compound 12, a new compound. Compounds 10 to 12 were all found to have negligible solubility in buffer thereby preventing any observation of their electrochemistry.

EXAMPLE 6

The literature abounds with papers describing the inclusion of ferrocenes into the hydrophobic activity of β-cyclodextrin (β-cd) resulting in a change in their physical properties not the least of which is an increase in their aqueous solubilities. A slight positive shift in the mid-point potentials of ferrocenes incorporated in β-cd has been reported (J. Org. Chem., 56 (1991) 35, Bioelectrochem. Bioenerg., 24 (1990) 257) and an inhibition by β-cd of the mediation of ferrocenes with GOD. There does not seem to be any report of β-cd hosting a manganese complex.

Figure 6:
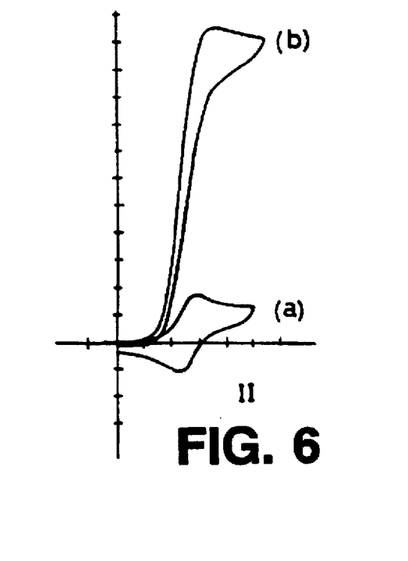
FIG. 6 comprises (a) a cyclic voltammogram of the β-cyclodextrin adduct of the manganese complex Compound 10, and (b) the catalytic wave upon addition of glucose oxidase.
Figure 7A:
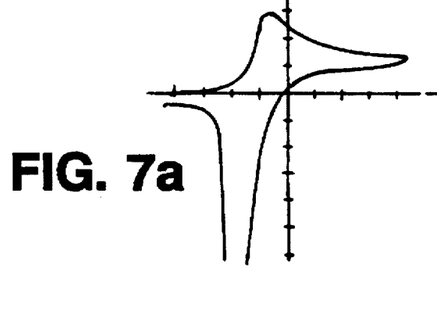
FIG. 7a–7d comprise cyclic voltammograms of the manganese complex Compound 16 in the presence of different amounts of β-cyclodextrin.
Figure 7B:
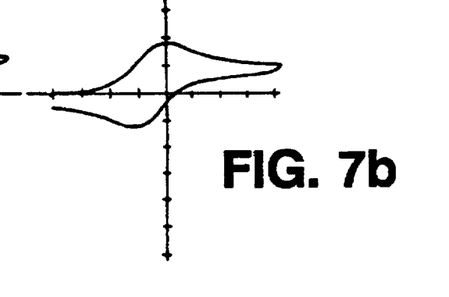
Figure 7C:
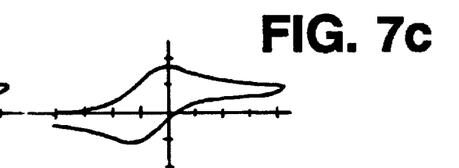
Figure 7D:
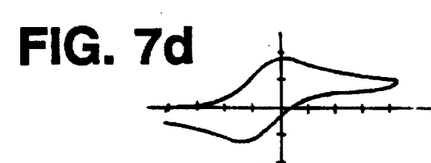

It was found that simply stirring the solid complex Compound 10 in an aqueous solution of β-cd at 70° C. resulted in the formation of a 1:1 inclusion complex which precipitated upon cooling of the mixture. The inclusion complex is soluble in PBS, to at least 0.5 mM. FIG. 6 comprises (a) a cyclic voltammogram of the β-cyclodextrin adduct of the manganese complex Compound 10 in 0.1 M glucose/PBS, and (b) the catalytic wave upon addition of 50 gl glucose oxidase. The inclusion complex displays a reversible wave at +255 mV with ΔEp=70 mV, and catalytic wave with $i_{cat}$=9.7µA is observed upon addition of GOD and glucose.

EXAMPLE 7

Having demonstrated that β-cd is capable of hosting a neutral manganese half sandwich complex, it was also found that β-cd might act as a solubilising agent for the insoluble oxidized form of the anionic complex Compound 16 mentioned earlier. The cyclic voltammogram of a 0.5 mM solution of Compound 16 in buffer has features which indicate that a species is being precipitated onto the electrode. However, addition of β-cd (0.5–5.0 mM) resulted in a reversible wave. FIG. 7a–d comprise cyclic voltammograms of the manganese complex Compound 16 in the presence of different amounts of (a) PBS only, and PBS containing (b) 0.5 mM β-cd, (c) 1.0 mM β-cd, and (d) 5.0 mM β-cd. The wave shows E½=+5 mV and Δ Ep=65mV.

EXAMPLE 8

Figures 8A, 8B:
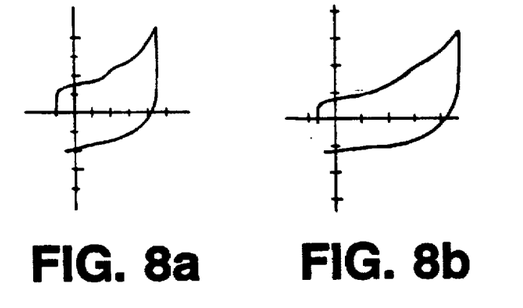
FIG. 8a–c comprise cyclic voltammograms of electrodes containing the manganese complexes (a) Compound 10, (b) Compound 11, and (c) Compound 12.
Figure 8C:
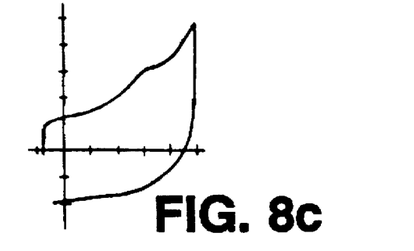
Figure 9A:
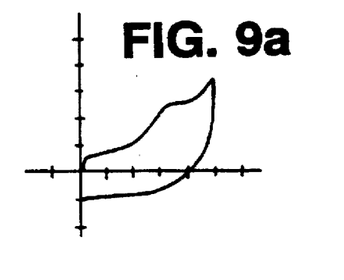
FIG. 9a comprise a cyclic voltammogram of electrodes containing the manganese complex Compound 10, and FIG. 9b comprises the catalytic wave upon addition of glucose oxidase.
Figure 9B:
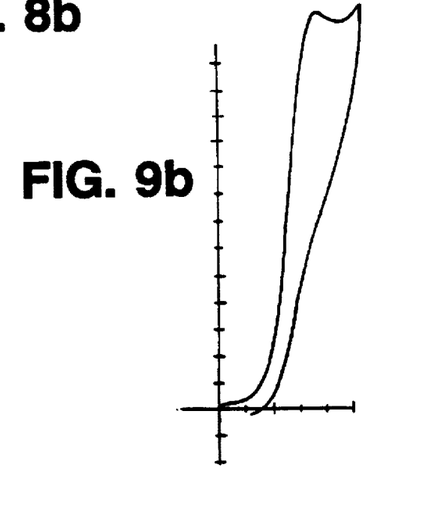

Further work with the dithiocarbamate complexes Compounds 10 to 12 was carried out with screen-printed carbon electrodes produced from carbon inks mixed with each of the complexes. As shown in FIG. 8a–c, oxidation waves were observed at +240, +300 and +290 mV for (a) Compound 10, (b) Compound 11, and (c) Compound 12, respectively, using scan rates of 50 and 100 mV/s at 0.5/μ/ cm. Catalytic currents in the region of 4 μA were recorded in the presence of GOD and glucose. Variable but increased currents of up to 29 μA were obtained with 0.1 M glucose when the enzyme was confined in the carbon electrode with the mediator, see FIG. 9.

Figure 10:
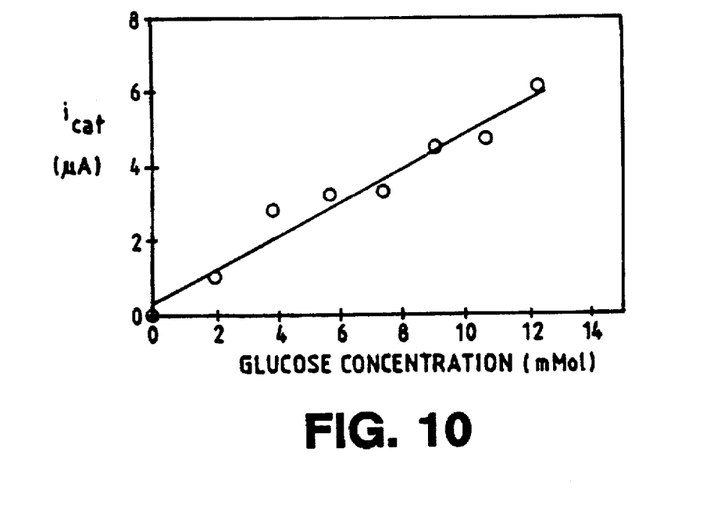
FIG. 10 shows the response to glucose of poised glucose oxidase/Compound 10 electrodes.

These mediator/enzyme electrodes responded linearly as shown in FIG. 10 to glucose in the range 0 to 12 mM when poised at +450 mV. Inclusion of ethylene glycol in the formulation of the carbon ink containing enzyme gave currents of up to 190 μA with 0.1 M glucose.

EXAMPLE 9

The ability of the β-cyclodextrin adduct of the manganese complex Compound 10 to mediate with horseradish peroxide (HRP) was assessed by comparing it with 1,1'-dimethylferrocene ethanolamine using rotating ring-disk voltammetry according to a literature method (Anal. Chem., 62 (1990) 2429). Experiments were carded out using a glass cell (14 ml capacity) containing a platinum counter electrode with a calomel reference electrode. A gold-gold ring-disk electrode, rotated at 4 Hz, was immersed in a phosphate-buffered saline solution of the mediator (0.5 mM) containing HRP (280 U). The catalytic ring current was then measured while poising the ring electrode at −100 mV and scanning the disk electrode from −100 to −600mV to generate hydrogen peroxide. Successive experiments with the ferrocene and the β-cd adduct of Compound 10 resulted in identical catalytic currents being recorded.

We claim:

1. A process of mediating electron transfer between an electrode and an oxidoreductase enzyme or other electron transfer redox protein using a mediator compound, wherein said mediator compound is a half-sandwich complex of a transition metal, said complex having only a single π-ligand with delocalised π bonding and having the general formula:

wherein the complex may be charged or neutral, π-ligand represents the single π-bonded ligand, M represents the transition metal atom, n is the number of ligands which are not π-ligands, and the n not-π-ligands are the same or different, are univalent or multivalent, and serve to satisfy the valency of the transition metal M.

2. The process of claim 1, wherein the π-ligand is selected from the group consisting of an allyl group, a cyclopropenyl group, a cyclobutadiene group, a cyclopentadienyl group, a benzene group, a cycloheptatrienyl group or a trimethylenemethane group.

3. The process of claim 1, wherein the π-ligand has 1 to 4 substituents selected from the group consisting of alkyl groups, alkoxy groups, amino and substituted amino groups, aminoalkyl and substituted aminoalkyl groups, a carboxylic acid group; and a sulphonic acid group.

4. The process of claim 1, wherein the transition metal M is iron, manganese or chromium.

5. The process of claim 1, wherein each not-π-ligand is selected from the group consisting of carbonyl, phosphine, isocyanide, nitrosyl, bipyridine, phenanthroline and dithiolate groups.

6. The process of claim 1, wherein the transition metal half-sandwich compound is employed as an inclusion complex in β-cyclodextrin.

7. An amperometric enzyme sensor for an analyte, which sensor employs a transition metal half-sandwich compound as the mediator, said half-sandwich transition metal half-sandwich compound including a transition metal complexed to only a single π ligand with delocalized π bonding and having the general formula:

wherein the complex may be charged or neutral, π-ligand represents the single-π-bonded ligand, M represents the transition metal atom, n is the number of ligands which are not π ligands, and the n not-π-ligands are the same or different, are univalent or multivalent, and serve to satisfy the valency of the transition metal M.

8. A disposable dry strip test element for an amperometric enzyme sensor, said disposable test element carrying a working electrode, test reagents comprising at least an oxidoreductase enzyme and a half-sandwich complex of a transition metal as the mediator for generation of a current indicative of the level of analyte, and a reference electrode, said complex having a single π ligand with delocalized π bonding and having the general formula:

wherein the complex may be charged or neutral, π-ligand represents the single-π-bonded ligand, M represents the transition metal atom, n is the number of ligands which are not π ligands, and the n not-π-ligands are the same or different, are univalent or multivalent, and serve to satisfy the valency of the transition metal M.

9. An electrically conductive printing ink which includes a half-sandwich complex of a transition metal as the mediator, said half-sandwich complex having a single π ligand with delocalized π bonding and having the general formula:

wherein the complex may be charged or neutral, π-ligand represents the single-π-bonded ligand, M represents the transition metal atom, n is the number of ligands which are not π ligands, and the n not-π-ligands are the same or different, are univalent or multivalent, and serve to satisfy the valency of the transitional metal M.

10. The amperometric enzyme sensor of claim 7, wherein the π-ligand is selected from the group consisting of an allyl group, a cyclopropenyl group, a cyclobutadiene group, a cyclopentadienyl group, a benzene group, a cycloheptatrienyl group or a trimethylenemethane group.

11. The amperometric enzyme sensor of claim 7, wherein the π-ligand has 1 to 4 substituents selected from the group consisting of alkyl groups, alkoxy groups, amino and substituted amino groups, aminoalkyl and substituted aminoalkyl groups, a carboxylic acid group; and a sulphonic acid group.

12. The amperometric enzyme sensor of claim 7, wherein the transition metal M is iron, manganese or chromium.

13. The amperometric enzyme sensor of claim 7, wherein each not-π-ligand is selected from the group consisting of carbonyl, phosphine, isocyanide, nitrosyl, bipyridine, phenanthroline and dithiolate groups.

14. The amperometric enzyme sensor of claim 7, wherein the transition metal half-sandwich complex is employed as an inclusion complex in β-cyclodextrin.

15. The dry strip test element of claim 8, wherein the π-ligand is selected from the group consisting of an allyl group, a cyclopropenyl group, a cyclobutadiene group, a cyclopentadienyl group, a benzene group, a cycloheptatrienyl group or a trimethylenemethane group.

16. The dry strip test element of claim 8, wherein the π-ligand has 1 to 4 substituents selected from the group consisting of alkyl groups, alkoxy groups, amino and substituted amino groups, aminoalkyl and substituted aminoalkyl groups, a carboxylic acid group; and a sulphonic acid group.

17. The dry strip test element of claim 8, wherein the transition metal M is iron, manganese or chromium.

18. The dry strip test element of claim 8, wherein each not-π-ligand is selected from the group consisting of carbonyl, phosphine, isocyanide, nitrosyl, bipyridine, phenanthroline and dithiolate groups.

19. The dry strip test element of claim 8, wherein the transition metal half-sandwich compound is employed as an inclusion complex in β-cyclodextrin.

20. The electrically conductive printing ink of claim 9, wherein the π-ligand is selected from the group consisting of an allyl group, a cyclopropenyl group, a cyclobutadiene group, a cyclopentadienyl group, a benzene group, a cycloheptatrienyl group or a trimethylenemethane group.

21. The electrically conductive printing ink of claim 9, wherein the π-ligand has 1 to 4 substituents selected from the group consisting of alkyl groups, alkoxy groups, amino and substituted amino groups, aminoalkyl and substituted aminoalkyl groups, a carboxylic acid group, and a sulfonic acid group.

22. The electrically conductive printing ink of claim 9, wherein the transition metal M is iron, manganese or chromium.

23. The electrically conductive printing ink of claim 9, wherein each not-π-ligand is selected from the group consisting of carbonyl, phosphine, isocyanide, nitrosyl, bipyridine, phenanthroline and dithiolate groups.

24. The electrically conductive printing ink of claim 9, wherein the transition metal half-sandwich compound is employed as an inclusion complex in β-cyclodextrin.

25. The electrically conductive printing ink of claim 9, wherein the transition metal M is iron.

26. The electrically conductive printing ink of claim 9, wherein the transition metal M is manganese.

27. The electrically conductive printing ink of claim 9, wherein the transition metal M is chromium.

28. The process of claim 1, wherein the transition metal M is iron.

29. The process of claim 1, wherein the transition metal M is manganese.

30. The process of claim 1, wherein the transition metal M is chromium.

31. The amperometric enzyme sensor of claim 7, wherein the transition metal M is iron.

32. The amperometric enzyme sensor of claim 7, wherein the transition metal M is manganese.

33. The amperometric enzyme sensor of claim 7, wherein the transition metal M is chromium.

34. The dry test strip of claim 8, wherein the transition metal M is iron.

35. The dry test strip of claim 8, wherein the transition metal M is manganese.

36. The dry test strip of claim 8, wherein the transition metal M is chromium.

* * * * *